US006472186B1

(12) United States Patent
Quintanar et al.

(10) Patent No.: US 6,472,186 B1
(45) Date of Patent: Oct. 29, 2002

(54) HIGH SPEED PROCESS AND APPARATUS FOR AMPLIFYING DNA

(76) Inventors: Andre Quintanar, 1744 L St., Apt. 1D, Lincoln, NE (US) 68508; R. Michael Nelson, 2649 N. 48th St., Apt. 3, Lincoln, NE (US) 68504

( * ) Notice: Subject to any disclaimer, the term of this patent is extended or adjusted under 35 U.S.C. 154(b) by 0 days.

(21) Appl. No.: 09/602,815

(22) Filed: Jun. 23, 2000

Related U.S. Application Data

(60) Provisional application No. 60/140,780, filed on Jun. 24, 1999.

(51) Int. Cl.$^7$ ................................................ C12P 19/34
(52) U.S. Cl. ........................ 435/91.2; 435/6; 435/91.1; 435/183; 435/287.2; 536/23.1; 536/24.33; 34/15
(58) Field of Search .................... 435/6, 91.1, 91.2, 435/183, 287.2; 536/23.1, 24.3, 24.33; 34/15

(56) References Cited

U.S. PATENT DOCUMENTS

| | | | |
|---|---|---|---|
| 3,616,264 A | 10/1971 | Ray et al. ................... 195/127 |
| 5,038,852 A | 8/1991 | Johnson et al. ............... 165/12 |
| 5,174,043 A | * 12/1992 | Yen ............................. 34/15 |
| 5,187,084 A | 2/1993 | Hallsby ....................... 435/91 |
| 5,200,313 A | * 4/1993 | Carrico .......................... 435/6 |
| 5,576,218 A | * 11/1996 | Zurek et al. ................ 436/174 |
| 5,602,756 A | 2/1997 | Atwood et al. .............. 364/500 |
| 5,616,301 A | 4/1997 | Moser et al. ................ 422/104 |
| 5,674,742 A | 10/1997 | Northrup et al. ......... 435/286.5 |
| 5,720,406 A | 2/1998 | Fassbind et al. ........... 220/23.4 |
| 5,720,923 A | 2/1998 | Haff et al. .................. 422/68.1 |
| 5,779,977 A | 7/1998 | Haff et al. .................. 422/68.1 |
| 5,783,439 A | 7/1998 | Reichler et al. .......... 435/286.1 |
| 5,795,547 A | 8/1998 | Moser et al. ................ 422/104 |
| 5,827,480 A | 10/1998 | Haff et al. .................. 422/68.1 |
| 5,856,194 A | 1/1999 | Arnquist et al. .............. 436/50 |

OTHER PUBLICATIONS

Hoffman, Les M., et al., "Use of a Gas Chromatograph Oven for DNA Amplification by the Polymerase Chain Reaction:", *BioFeedback*, Agrigenetics Advanced Science Company Manscript No. 89, 1988.

Northrup, M. Allen, et al., "A Miniature Integrated Nucleic Acid Analysis System", Automation Technologies for Genome characterization, 1997, pp. 189–204.

* cited by examiner

Primary Examiner—B. L. Sisson
(74) Attorney, Agent, or Firm—McKee, Voorhees & Sease, P.L.C.

(57) ABSTRACT

The Polymerase Chain Reaction (PCR) is one of the most widely used techniques in molecular biology (U.S. Pat. No. 4,683,202 to Mullis). In general, most thermocyclers which automate the PCR nucleic acid amplification process rely upon programmable heat blocks with a large thermal mass. Consequently, most of the time in an automated PCR cycle is spent non-productively in transition between denaturation, annealing, and elongation temperatures. Recently, much faster hot-air thermocyclers have been constructed which shorten these transition times, allowing 30 cycles of PCR in 10 to 30 minutes. While elegant in principle, the design of these systems is not optimal. Air is a relatively poor heat transfer medium; and the operation of a single heat/reaction chamber at atmospheric pressure is inherently slow. Much faster thermocyclers can be constructed using pressurized gas delivered to a thermostated reaction chamber by computer-controlled electronic valves. A novel process, high-speed gas phase PCR, is described. This process has been successfully automated using a novel thermocycing device, which has been successfully to amplify DNA from picogram to microgram amounts in ~1 to 5 minutes.

18 Claims, 12 Drawing Sheets

Thermal Conductivity of Gases at 0°C
*(Values near P = 1 Atm, taken from Johnston & Grilly, 1946; Bosworth, 1952; and Azbel, 1984)*

| Gas | Chemical Symbol | Molecular Mass | Thermal Conductivity k (Watts/meter-°C) |
| --- | --- | --- | --- |
| Hydrogen | $H_2$ | 2 | 0.175 |
| Helium | He | 4 | 0.141 |
| Neon | Ne | 20 | 0.046 |
| Methane | $CH_4$ | 16 | 0.030 |
| Air | (mostly $N_2$) | ~28 | 0.024 |
| Argon | Ar | 40 | 0.016 |
| Carbon dioxide | $CO_2$ | 46 | 0.015 |

*Fig. 1*

HIGH SPEED PROCESS AND APPARATUS FOR AMPLIFYING DNA

CROSS REFERENCE TO RELATED APPLICATIONS

This application claims priority from co-pending U.S. Provisional patent Application Serial No. 60/140,780, filed Jun. 24, 1999.

GRANT REFERENCE

This invention was described in a Small Business Innovation Research (SBIR) grant application submitted to the National Institutes of Health on Dec. 15, 1998. According to 37 CFR §401 and Section 5 of the United States Public Health Service 1998 Omnibus Solicitation for SBIR Grants, the U.S. Government may have certain rights in this invention.

BACKGROUND OF THE INVENTION

1. Field of the Invention

The invention relates to a high-speed process for amplifying DNA, and a companion apparatus for automating this process, based upon the Polymerase Chain Reaction (PCR). Specifically, the present invention relates to a process in which pressurized gas is used to heat and cool a biochemical reaction chamber. This novel process has been successfully automated, as demonstrated by its ability to amplify DNA from picogram to microgram quantities on an unprecedented time scale.

2. Significance

Anyone who has ever driven an automobile or flown in a jet airplane can attest to the speed and reliability of pressurized gas machines. Pressurized gas devices include internal combustion engines, jet turbines, rockets, pneumatic airtools, and gas chromatographs. However, gas machines are not widely used in biochemistry. Described herein is a novel process for high-speed Polymerase Chain Reaction amplification of DNA, which relies upon the use of a pressurized gas thermocycler with high speed valves.

Five features of this pressurized gas thermocycler are important: (1) It is the fastest automated PCR device ever built; 30 cycles of amplification of an 85 base pair (b.p.) DNA fragment were carried out in 78 seconds. (2) With proper engineering, it can be made even faster. (3) It is compatible with on-line, fluorescent dye-based DNA detection optics. (4) Unlike any device which has been previously described, the speed of DNA thermocycling is limited by the biochemistry rather than the dead time of the thermocycler. In high-speed gas phase PCR, the rate of Taq Polymerase elongation (~80 nucleotides/sec at 72° C.) is rate-limiting. Theoretically, if faster DNA Polymerases (>1000 nucleotides/sec) can be found which are compatible with high-speed gas phase PCR, then even faster thermocycling times (<10 sec/30 cycles) are possible. (5) As an added benefit, high-speed gas phase PCR is generally more accurate than slower methods, probably because false reaction products have so little time to anneal and/or elongate.

Pressurized gas thermocyclers should prove especially useful in the diagnosis of life-threatening diseases where speed is essential. The present invention has major implications for DNA-based diagnoses used in biomedical research, genetics, molecular medicine, agriculture, veterinary science, and forensics.

3. The Background Art

[a] The Polymerase Chain Reaction. In order to understand how and why pressurized gas thermocyclers were built, one must first understand the Polymerase Chain Reaction (PCR) and how it has previously been automated. The Polymerase Chain Reaction is one of the most widely used techniques in molecular biology (U.S. Pat. No. 4,683,202 to Mullis; Saiki et al., 1985; Erlich, 1989; Mullis et al., 1994). PCR-amplified DNA can be used to diagnose mutations responsible for human genetic diseases (Kogan et al., 1987), in blood and tissue typing (Saiki et al., 1989a), or to detect pathogens responsible for important infectious diseases (Persing et al., 1993).

In a typical PCR reaction, template DNA sequences lying between the ends of two defined oligonucleotide primers can be amplified in 1 to 2 hours. Three sequential steps are normally employed: (i) double-stranded DNA is denatured (D) to a single-stranded form at a high temperature (90° C. to 95° C.), (ii) the resulting single-stranded DNA strands are annealed (A) to oligonucleotide primers at ~40° C. to 60° C., and (iii) primer template complexes are elongated (E) using a thermostable DNA Polymerase such as *Thermus aquaticus* (Taq) Polymerase at ~72° C. (Saiki, 1989b).

One cycle of these three steps (denaturation/annealing/elongation) results in a two-fold amplification of a DNA fragment whose 5' and 3' ends are defined by sequence-specific annealing of the oligonucleotide primers to the DNA template. Therefore, 30 PCR cycles result in a $2^{30}$-fold (~$10^6$-fold) amplification of a particular DNA sequence. DNA is thus amplified from picogram to microgram amounts, which can be detected by standard analytical methods, such as gel electrophoresis, DNA hybridization, or optically.

[b] Automated PCR Instruments. A variety of machines have been built which automate the three-step PCR amplification process (Oste, 1989; Oste, 1994; Newton, 1995; Johnson, 1998). Generally, these devices may be classified into two categories: robotic devices which move the DNA samples to the heat; and thermocyclers which bring the heat to the samples.

Robotic devices such as Stratagene's ROBOCYCLER move tubes containing PCR reaction samples to and from a series of heat baths, which are thermostated at different temperatures. Although these devices may be useful in certain research applications, they are incapable of high-speed PCR. They require >60 minutes for 30 cycles of amplification.

Since the late 1980s, thermocyclers have become familiar devices in many biochemistry laboratories. Most commercially available PCR devices (Perkin-Elmer, MJ Research, Ericomp, Techne, Eppendorf, BioRad, Hybaid) are thermocyclers (Johnson, 1998). In general, two types of thermocyclers are employed: programmable heat blocks and hot-air thermocyclers.

[c] Programmable Heat Blocks. Most thermocyclers resemble "waffle irons." They are heat blocks with holes in them where plastic reaction tubes are heated and cooled under electronic control. Several such devices have been described by Johnson (1998). The problem with this type of design is that one spends most of ones' time waiting for a block of metal to heat up or cool down. Like the waffle chef—who spends most of his time heating up the waffle iron beforehand, or cooling it off afterwards—very little time is spent actually cooking the waffles. For example, in the MJ Research PTC-150 thermocycler (Watertown, Mass.), 14 seconds/cycle is lost in transition between D, A, and E temperatures (~94° C., 55°, and 72°).

Many commonly employed PCR protocols spend one minute at 94° C. (denaturation), one minute at ~55° C.

(annealing), and one minute at 72° C. (elongation). For example, in the original PCR method used by Cetus workers (Saiki et al., 1989b), a 536 b.p. β-globin DNA fragment was amplified using 30 cycles of (1 min at 94° C., 1 min at 55° C., 1 min at 72° C.). The active duty time for this thermocycling protocol is only ~3.5 minutes=210 seconds. This is the time needed to enzymatically copy a 536 b.p. template 30 times at an elongation rate of ~80 nucleotides/sec (Innis et al., 1988; Gelfand and White, 1990).

Commercially available heat block thermocyclers (Perkin-Elmer, Ericomp, MJ Research, Eppendorf, Techne, BioRad, Snark Technologies) require 20 to 25 seconds to cool from 94° C. to 55° C. and another 14 to 20 seconds to heat from 55° C. to 94° C. (Johnson, 1998). Therefore, the "dead time" for each PCR cycle is another 40±5 seconds per cycle. As shown in FIG. 4, commonly employed thermocycling protocols require (220 seconds/cycle×30 cycles)=6600 seconds=110 minutes (Saiki et al., 1989b). Only ~3.5 minutes of this ~2 hours is productively focused on the PCR process.

[d] Hot-Air Thermocyclers. In order to overcome the long transitional dead times of heat blocks, hot-air thermocyclers have been constructed which allow 30 cycles of PCR amplification to be carried out in as little as ~10 to 30 minutes. Wittwer and his colleagues have carried out considerable engineering groundwork to optimize rapid DNA amplification in hot-air PCR thermocyclers (Wittwer et al., 1989; Wittwer and Garling, 1991; Wittwer et al., 1994). The rate-limiting step in the three-step PCR reaction sequence (denaturation/annealing/elongation) is the rate of DNA Polymerase elongation. At an elongation rate of 80 nucleotides/sec by Taq Polymerase (Innis et al., 1988; Gelfand and White, 1990), less than one second per cycle is actually needed to amplify DNA fragments shorter than 100 b.p. using ~20 mer primers. For example, only about five seconds per cycle were needed to copy a 536 b.p. β-globin amplicon through 30 PCR cycles (Idaho Technology, 1995).

In commercial hot-air thermocyclers, first built by Idaho Technology (Idaho Falls, ID), the reaction time needed for one PCR cycle of denaturation/annealing/elongation was substantially reduced because: (i) the device had very low thermal mass; (ii) gaseous phase heat transfer from hot-air to the aqueous reaction was carried out in thin-walled capillary tubes; and (iii) the denaturation and annealing times during the PCR cycle were minimized. Using a PCR protocol of 30 cycles of [0 sec 94° C. (denaturation), 0 sec 55° C. (annealing), 5 sec 72° C. (elongation)], a 536 b.p. β-globin DNA fragment was amplified in 9.9 minutes (Idaho Technology, 1995). This rapid hot-air thermocycling protocol was therefore ~220/19.8=11 times faster than the original protocol of Saiki et al. (1989b) for PCR amplification of a 536 b.p. β-globin DNA fragment in a conventional heat block thermocycler. Although the design of hot-air thermocyclers of Wittwer et al. (U.S. Pat. No. 5,455,175; Wittwer et al., 1990; 1994) is admirable, it is not optimal.

First of all, Wittwer et al. (1990) have stated that "Air is an ideal heat transfer medium which can change temperature quickly because of its low density." This statement is demonstrably incorrect. Heat transfer by conduction is described by the Fourier Equation:

$$q=-kA[dT/dx]$$

where q is the heat flux, k is the heat transfer coefficient, A is the surface area, and dT/dx is the thermal gradient. This mistake is repeated by Zurek et al. (1996; U.S. Pat. No. 5,576,218) who also rely exclusively on forced hot air as a heat transfer medium.

The basic laws governing heat transfer in the gas phase have been known since Fourier (1822) and are taught in standard mechanical engineering textbooks (Bosworth, 1952; Azbel, 1984; Chapman, 1984). For a given thermal gradient dT/dx in a thermodynamic system of fixed surface area A, the heat flux q is directly proportional to the heat transfer coefficient k; in other words, dT/dx=-q/kA. The negative sign indicates that heat is lost from the system. The heat transfer coefficient of helium was measured by Ubbink (1947) and is listed in tables published by Johnston and Grilly (1946), Bosworth (1952), Azbel (1984), and Chapman (1984). As shown in FIG. 1, helium has a heat transfer coefficient seven times that of air. Neon transfers heat about twice as fast as air.

Therefore, prior art hot-air thermocyclers use the wrong gas for rapid heat transfer. Among the non-combustible gases, air is available; helium is optimal. U.S. Pat. No. 5,455,175 to Wittwer et al. incorrectly assumes that the same gas (air) should be used for heating the reaction chamber, cooling the chamber, or holding its temperature at a fixed value. In fact, as shown in the temperature versus time profile in FIG. 8b, high k gases, such as helium, are superior for heating/cooling the reaction chamber, whereas low k gases, such as air or $CO_2$, afford better thermal control when holding the temperature for several seconds during elongation at ~72° C. (see FIG. 5b and 8b). In other words, different gases are optimal for different steps of the PCR process.

Secondly, U.S. Pat. No. 5,455,175 to Wittwer et al. and U.S. Pat. No. 5,576,218 to Zurek et al. specify the use of air (but no other gas) at atmospheric pressure (but no other pressure) for gas phase PCR. Not only is air a relatively poor heat transfer gas, but it need not be used at atmospheric pressure. Gas phase PCR at atmospheric pressure is convenient; but the process is orders of magnitude faster at elevated pressure (P>1 atm; see FIGS. 4, 5b and 8b).

For example, in the forced hot-air thermocycling process of Zurek et al. described in U.S. Pat. No. 5,576,218, "the sample could be heated from 50° C. to 85° C. within 12 to 15 seconds . . . by injecting cooling air at a substantially lower temperature than the target temperature, for example 22° air, the sample was cooled from 85° C. to 50° C. in approximately 60 to 75 seconds." Therefore, the method of Zurek et al. described in U.S. Pat. No. 5,576,218 requires at least (12+60)=72 seconds per cycle just to heat and cool the gas (air), regardless of whether any useful biochemistry has taken place. In the present invention (see FIGS. 8a and 8b), 30 cycles of PCR amplification are achieved in as little as 78 seconds—about the same time needed for one cycle using the method of Zurek et al. described in U.S. Pat. No. 5,576,218.

Third, it has been unnecessarily assumed by Wittwer et al. (U.S. Pat. No. 5,455,175; Wittwer et al. 1990; 1994) that the heat chamber and reaction chamber are the same thing (see FIG. 2).

Altogether, for efficient heat transfer in the gas phase, hot-air thermocyclers utilize the wrong gas, wrong pressure, and wrong configuration of heat chamber to reaction chamber. Much faster gas phase thermocyclers can be designed using pressurized gas, particularly pressurized helium.

OBJECTS OF THE INVENTION

A process for amplifying DNA using pressurized gas and electronic valves has not been previously described. Both the high-speed pressurized gas amplification process and a companion apparatus for its automation are the primary objects of the present invention.

Specifically, in view of the above described state of the art, the present invention seeks to realize the following objectives.

It is an object of the present invention to provide a process for amplifying DNA so that Polymerase Chain Reaction (PCR) amplification of DNA can be carried out rapidly in the gas phase. In this process, hot or cold pressurized gases are delivered to a physically separate reaction chamber containing biological samples, in order to control the temperatures used for DNA denaturation, primer: template annealing, and polymerase-catalysed elongation.

It is a further object of the invention to provide for a process for subjecting biological samples to rapid thermocycling, by regulating the flow of hot or cold pressurized gas to these samples.

It is another object of the present invention to provide an apparatus suitable for carrying out gas phase amplification of DNA, using microprocessor-controlled electronic valves to regulate the flow of hot or cold pressurized gas into a thermostated biochemical reaction chamber.

It is also an object of the present invention to provide an apparatus which can subject a biological sample to rapid thermal cycling, using one or more gases at a pressure greater than one atmosphere.

It is also an object of the present invention to provide an apparatus which can subject a biological sample to rapid thermal cycling, in which pressurized air, helium, carbon dioxide, nitrogen, or argon are employed as gas phase heat transfer media.

Finally, it is an object of the present invention to provide an apparatus in which a physically separated gas heating chamber and reaction chamber are employed.

Some of the major advantages of the invention are as follows: First, the invention decreases the time needed for amplification of DNA using the Polymerase Chain Reaction by one to two orders of magnitude over any previously described process or device (see FIG. 8b). Second, the process is inherently more accurate than slower procedures, since false reaction products have practically no time to anneal and/or elongate (see FIGS. 5a, 6, 7 and 8a). Third, thermal control is as good or better than conventional heat block or hot-air thermocyclers (see FIG. 5b and 8b). Fourth, high-speed gas phase PCR is a very reliable process. Except for the electromechanical relays and valves, no moving parts are employed. Fifth, the high-speed gas phase PCR process is fully compatible with on-line detection optics, so that rapid (~1 minute) DNA amplification/detection can be carried out. The invention therefore affords rapid, accurate, and reliable DNA amplification and detection on an unprecedented time scale.

SUMMARY OF THE INVENTION

The present invention includes a high-speed process for amplifying DNA. A reaction chamber containing a biological sample, a DNA polymeras, oglionucleotide primers, and deoxynucleotide precursors is provided. The reaction chamber accepts the flow of one or more heat transfer gases. A first heat transfer gas is heated in a heating chamber which is physically separated from the reaction chamber. The heated gas is delivered to the reaction chamber at a pressure greater than the reaction chamber pressure. Heat from the heated gas is utilized to denature DNA. A second heat transfer gas, which may be the same kind as, or a different kind of gas, than the first heat transfer gas is delivered to the reaction chamber. The second heat transfer gas cools the reaction chamber to a temperature low enough to allow the denatured DNA to anneal to the oglionucleotide primers. Finally, the temperature of the reaction chamber is increased to a sufficient temperature to allow for elongation of primer:template complexes.

When hot or cold gas is delivered to a biochemical reaction chamber under the control of microprocessor-controlled electronic valves, extremely fast thermocycling is possible. By delivering, alternately, bursts of hot and cold gas to a thermostated reaction chamber, the temperature of an enzyme-catalysed reaction can be controlled. Ideally, the gas of choice is helium, but for convenience, other gases can also be employed.

The present invention can also include an apparatus for high-speed amplification of DNA. The apparatus includes a reaction chamber having a pressure, usually normal room or atmospheric pressure. A heating chamber, which is physically separated from the reaction chamber, is fluidly connected to the reaction chamber. A first container, having a heating gas at a pressure greater than the reaction chamber pressure, is fluidly connected to the heating chamber. A second container, having a cooling gas (which may be the same kind or different kind of gas as the heating gas), is fluidly connected to the reaction chamber. A cooling gas inlet valves is positioned between the second container and the reaction chamber, and a heating gas inlet valve is positioned between the first container and the reaction chamber. A programmable controller, having inputs and outputs, is used to control opening of the inlet valves. A temperature sensor is connected to an input of the controller. The controller opens and closes the inlet valves to reach or maintain a desired temperature within the reaction chamber.

If the temperature of an optimal heat transfer gas, such as helium, is raised in a chamber which is physically separated from the reaction chamber, and then delivered to the reaction chamber, then extremely fast thermocycling is possible. Even faster heat transfer is possible if cold gas is delivered to the chamber. For automated heating and cooling of the reaction chamber, preferably at least two electronic valves (hot gas valve and cold gas valve) and one or more mechanical relief valves are employed.

The design of our pressurized gas thermocycler differs in five important ways from prior art hot-air thermocyclers: (i) An optimal heat transfer gas (helium) can be employed for rapid heating/cooling of the reaction chamber. For convenience, other gases, such as air or $CO_2$, can also be used, although heat transfer is not as fast as when helium is employed. (ii) The heat chamber and reaction chamber are physically separated in space (heat chamber≠reaction chamber). (iii) Microprocessor-controlled electronic valves are used to deliver pre-heated gas or pre-cooled gas to the reaction chamber. (iv) Gas is delivered to the reaction chamber at elevated pressure (>1 atm), but the biochemical reaction is sealed in a thin-walled capillary tube in which the pressure is unchanged. (v) Unlike any other thermocycler which has been preciously described, the rate-limiting step in the pressurized gas thermocycler (~1 sec/cycle) is a biochemical step (the rate of DNA Polymerase elongation) rather than the dead time of the machine itself. In fact, the pressurized gas thermocycler is so fast that, if faster thermostable DNA polymerases (>100 nucleotides/sec) were available, then 30 cycles of PCR could be carried out in less than one minute. Pressurized gas thermocyclers, but no other known devices, are capable of such high-speed DNA amplification.

In practice, it is not necessary to use pressurized helium gas for both heating and cooling the reaction chamber. Bottled pressurized carbon dioxide ($CO_2$) gas expands and cools upon leaving its storage container. It is therefore convenient to use pressurized helium gas to heat the reaction chamber and bottled $CO_2$ gas to cool the chamber.

For example, using hot (~180° C.) pressurized helium gas and cold (~5° C.) pressurized $CO_2$ gas, which are delivered to a thermostated reaction chamber via 5V electronic valves and digital relays, it is possible to cyclically change the temperature from 92° C. (DNA denaturation temperature) to 55° C. (primer annealing temperature) to 72° C. (DNA polymerase elongation temperature) in less than 2.7 seconds. With slight losses to machine dead time, 30 cycles of 92° C./55° C./72° C. can be carried out in 1.3 to 2.3 minute when minimal (0 to 2 sec) D, A, and E times are used.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 1 is a table of Thermal Conductivity of Gases, with thermal conductivity units (k-values) expressed in Watts/meter-° C.

FIG. 3b is a perspective view of the back of the reaction chamber, as seen in FIG. 3a.

FIG. 3c is a cross-sectional view of the reaction chamber takes along line 3c—3c in FIG. 3a.

FIG. 5b is a temperature versus time profile of the DNA amplification reactions shown in FIG. 5a.

FIG. 8b is a temperature versus time profile of the DNA amplification reactions shown in FIG. 8a.

DETAILED DESCRIPTION OF THE INVENTION

The present invention will be described as it applies to an exemplary embodiment. It is not intended that the present invention be limited to the described embodiment. It is intended that the invention cover all modifications and alternatives which may be included within the spirit and scope of the invention.

Diligent development of this invention has proceeded in three stages: (1) design of the pressurized gas thermocycler, (2) fabrication and optimization of the device, and (3) use of the device and process in high-speed PCR amplification experiments.

1. Design of a High-Speed Pressurized Gas Thermocycler

We wished to build a pressurized gas thermocycler which would carry out high-speed PCR amplification of DNA by injecting hot or cold gas into a thermostated reaction chamber under the control of fast (<15 msec/cycle) electronic valves, digital relays, and a microprocessor controller. Ideally, this device would contain a minimum number of moving parts and be compatible with optics used for detection of fluorescent dye-labeled DNA (Higuchi et al., 1992; Haugland, 1996).

In particular, we designed a device in which the temperature could be rapidly changed by injecting hot and cold pressurized gas into a reaction chamber under electronic control, using digitally programmable "hot gas" and "cold gas" valves. The pressure in the reaction chamber is maintained at a relatively constant value by means of a mechanical relief valve, although the temperature can be changed upon demand. Reaction samples (10 to 20 microliters in volume) are sealed in thin-walled capillary tubes as described by Wittwer and Garling (1991). Therefore, although the pressure inside the reaction chamber varies, the pressure in the capillary tubes remains unchanged.

Figure 2:
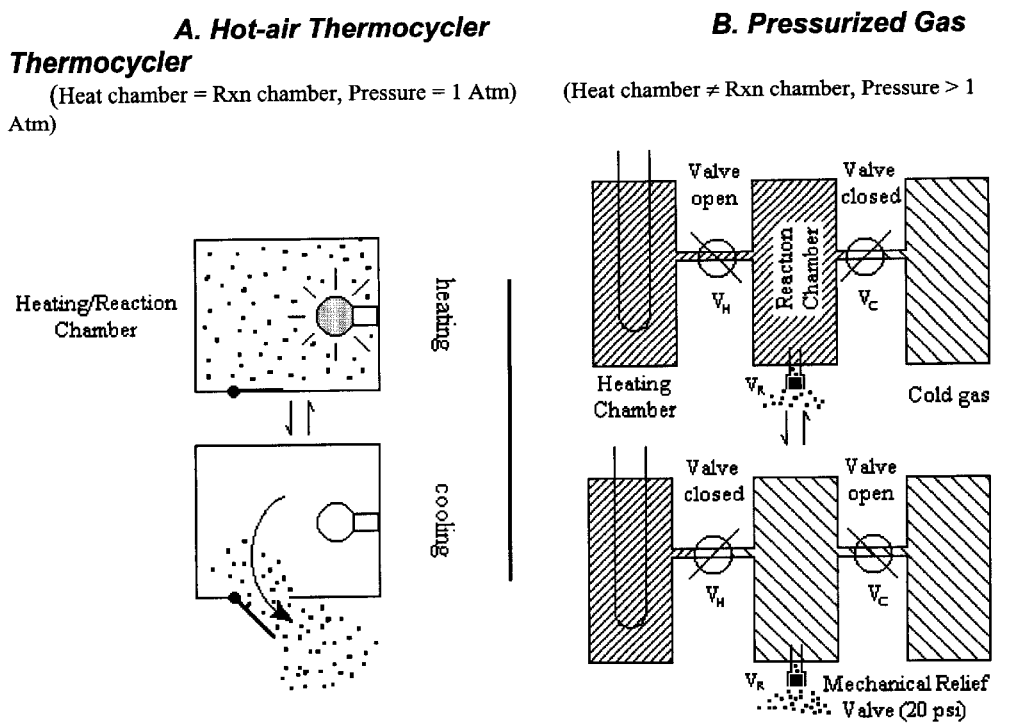
FIG. 2 is a schematic comparison of a hot-air thermocycler and a pressurized gas thermocycler.

A pressurized gas thermocycler differs from a hot-air thermocycler (U.S. Pat. No. 5,455,175 to Wittwer et al.) in several important respects, as shown in FIG. 2. In the hot-air thermocycler (FIG. 2a), a single reaction chamber with a heat lamp is used to heat air and to carry out PCR reaction (heat chamber=rxn chamber). In the pressurized gas thermocycler (FIG. 2b), three separate chambers are used: a heating chamber, a cold gas supply chamber, and a reaction chamber. In order to heat samples in the reaction chamber, pre-heated gas from the heat chamber is delivered under pressure to the reaction chamber by electronic valve $V_H$ (hot gas valve 20). In order to cool samples in the reaction chamber, cold gas is delivered under pressure to the reaction chamber by electronic valve $V_C$ (cold gas valve 21). A mechanical relief valve $V_R$ (18 in FIG. 3a) allows exit of pressurized gas from the reaction chamber.

2. Fabrication and Optimization of a Pressurized Gas Thermocycler

Reference will now be made to the drawings wherein like structures will be provided with like reference designations. Schematic drawings of the pressurized gas thermocycler and its reaction chamber are shown in FIGS. 3a, 3b, and 3c.

Figure 3A:
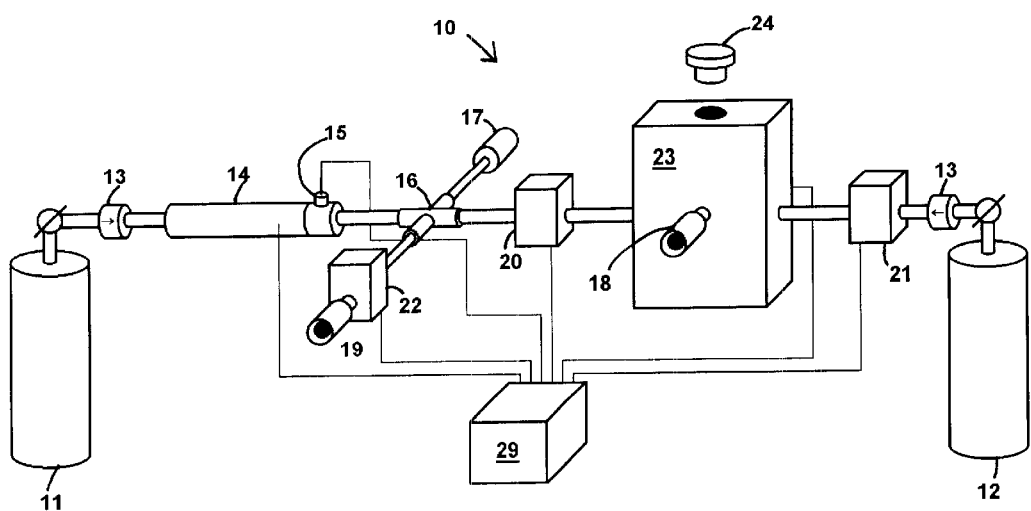
FIG. 3a is a perspective view of an embodiment of an apparatus to amplify DNA according to the present invention.

As seen in FIG. 3a, the thermal cycling device 10 includes a reaction chamber made of insulating (low k) material, generally designated at 23, which is adapted to accept samples to be introduced through a closing cap 24. Preferably, reaction chamber 23 has k value of less than 0.5 Watts/centimeter-degree K. Reaction chamber 23 can be comprised of a number of different materials, such as stainless steel or titanium. Polyurethane or polymethane plastics with ceramic binders, sold under trade names such as VESPEL, TORLON, and BUTTERBOARD (which is manufactured by Golden West of Calif.), can also be used as a reaction chamber 23 material. Cold gas supply 12 is separated from reaction chamber 23 by a one-way check valve 13 (available from Linweld of Lincoln, Nebr.) and an electronic valve 21 (a 5 VDC valve manufactured by Spartan Scientific of Ohio) which is actuated by a digital relay operated by controller 29. Controller 29 can be a microprocess or programmable logic controller (PLC), such as a Micro-485 manufactured by Blue Earth of Mankato, Minn. Hot gas supply 11 is connected to a process heater 14 (500

Watt process heater manufactured by Hotwatt of Danvers, Mass.) using a one-way check valve 13. Process heater 14 is actuated by a heavy-duty relay operated by controller 29 according to thermal sensor 15 (manufactured by Physitemp of New Jersey) which monitors the temperature of the heated gas. Hot gas exiting the heater 14 flows from connecting cross 16 through an electronic valve 20 (operated by controller 29) into the reaction chamber 23. The process heater requires a continuous flow of gas whenever valves 20 and 22 are closed; therefore a mechanical relief valve 17 (30 p.s.i.) is connected to the cross 16. The system pressure and flow of hot gas into the reaction chamber 23 can be reduced by opening the throttle valve 22 (operated by controller 29), which is connected to a mechanical relief valve 19. Mechanical relief valves 18 and 19 have the same cracking pressure (20 p.s.i.). Therefore, when valve 22 is open, the hot gas flow rate and pressure entering the chamber 23 are reduced.

Figure 3B:
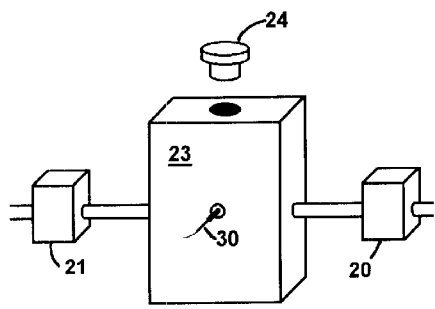
Figure 3C:
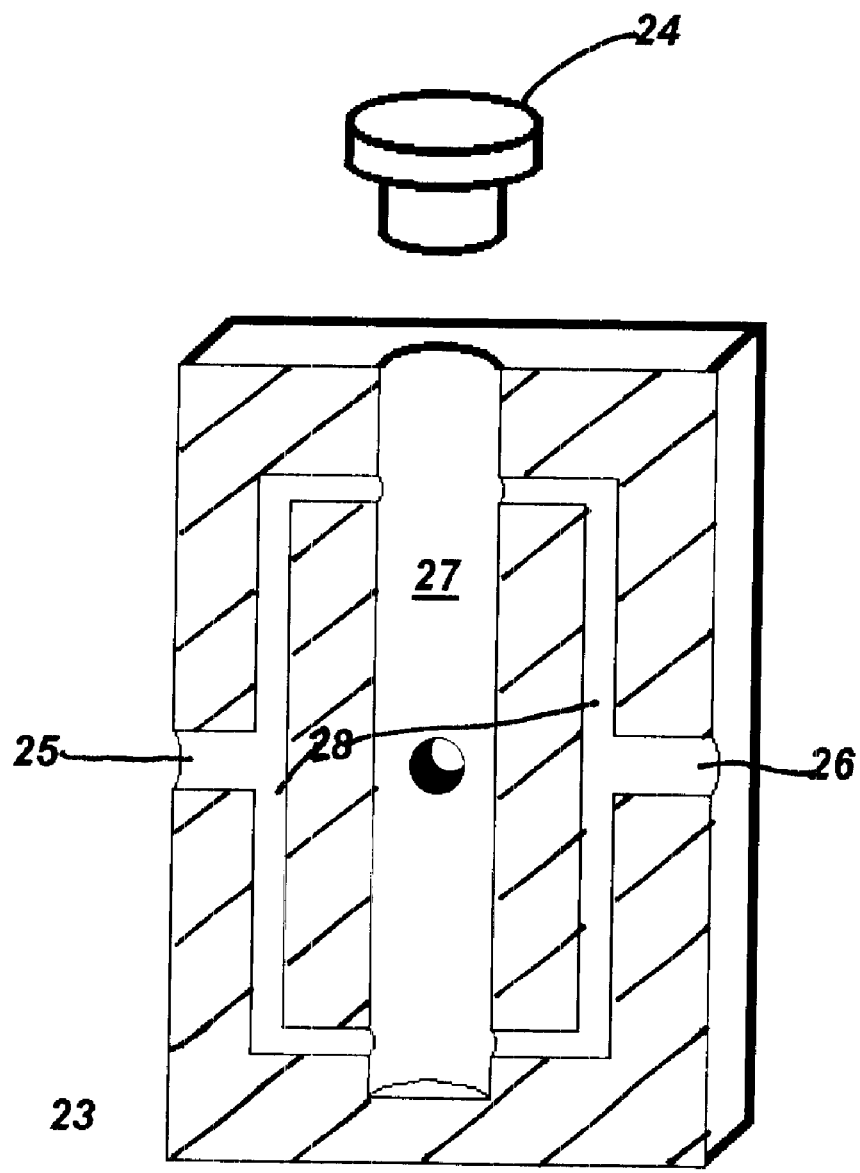

As shown in FIG. 3b, valves 20 and 21 can be opened or closed upon demand, using controller 29, based upon the temperature in the reaction chamber 23 measured by the thermocouple 30.

As shown in FIG. 3c, the reaction chamber 23 contains a central cavity 27, which contains reaction samples sealed in thin-walled capillary tubes. Hot gas enters the chamber from hot gas valve port 25, passes through flow conditioner 28 into the central cavity 27. Cold gas enters the chamber from cold gas valve port 26, passes through flow conditioner 28 into central cavity 27. The flow conditioner 28 helps maintain the desired temperature of the reaction chamber 23. Gas exits the reaction chamber 23 through mechanical relief valve 18.

It is preferable to be able to hold temperature in the reaction chamber to within about ±1° C. for accurate primer: DNA annealing and Taq Polymerase elongation. In order to do so, a third valve was added, a so-called throttle valve (22 in FIG. 3a), which made it possible to drop the system pressure during elongation steps. This tri-valve device (hot gas valve, cold gas valve, throttle valve) was found to give excellent thermal control.

The tri-valve pressurized gas thermocycler was tested with various combinations of hot and cold supply gases. In general, pressurized air is available, inexpensive, and easy to control. On the other hand, pressurized helium gas is a superior heat transfer gas (FIG. 1), but is more problematic with respect to thermal control (FIG. 8b).

Figure 9:
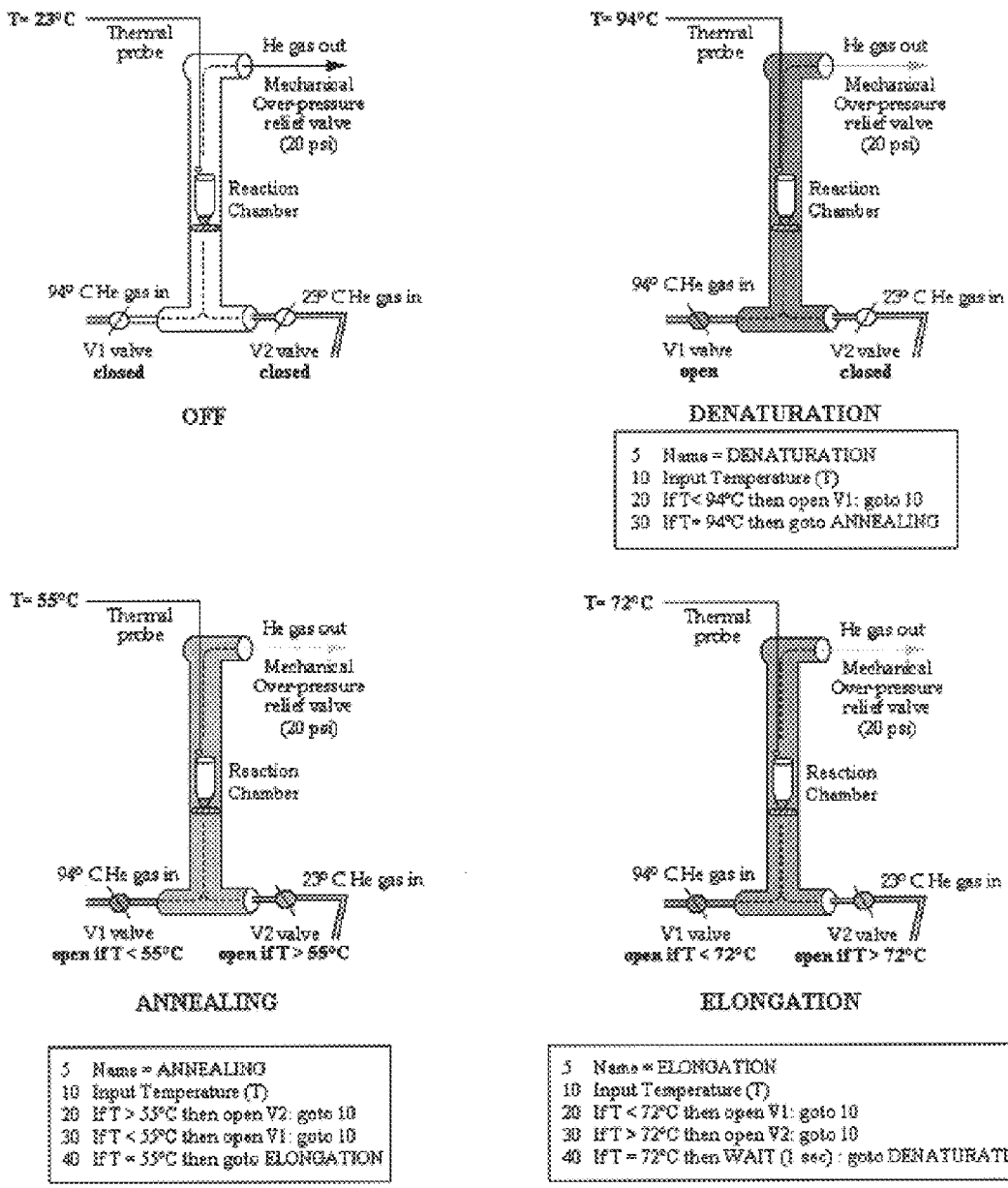
FIG. 9 is schematic diagram, which shows the basic operational stages of the apparatus of FIG. 3c.

Operation of the pressurized gas therrnocycler is outlined schematically in FIG. 9. There are basically three operating modes, which are controlled by activating relays wired to the valves: (1) heating the reaction chamber, (2) cooling the reaction chamber, and (3) holding the temperature of the reaction chamber.

In order to increase the temperature of the reaction chamber 23, the hot gas valve 20 is OPENED, so that hot pressurized gas is delivered to the chamber. The cold gas valve 21 and throttle valve 22 remain CLOSED.

In order to reduce the temperature of the chamber, the hot gas valve 20 is CLOSED, the cold gas valve 21 is OPEN, and the throttle valve 22 is CLOSED.

During the elongation step of the PCR process, when the temperature is held near 72° C., the cold gas valve 21 is CLOSED, the throttle valve 22 regulating the system pressure and gas flow rate is OPEN and the hot gas valve 20 is OPEN or CLOSED upon demand based on the temperature measured by the thermal sensor 30 located in the reaction chamber 23. This valve configuration provides superior thermal control for holding the temperature near a preset value.

The opening and closing of hot, cold, and throttle valves is controlled by electrical signals from the system controller to electrical relays which actuate the valves. The system control software determines the opening and closing of these valves.

When different "hot" or "cold" supply gases are employed, modified software is utilized, since gas flow and mixing in the chamber varies, depending upon the gas mixtures chosen. It is convenient to use either pressurized air or helium as a "hot" gas; and to use air or $CO_2$ as a "cold" gas; but a variety of different gases can be employed. It is neither necessary nor optimal to use the same gas to heat, cool, or hold the temperature of the chamber.

As shown below (FIGS. 5a, 6, 7, and 8a) high-speed gas phase PCR amplification of DNA can be carried out using pressurized air (or helium) as a 'hot' gas; and pressurized $CO_2$ as a 'cold' gas. Thirty cycles of PCR amplification can be achieved in 78 to 335 seconds, depending upon the heat transfer gases chosen. In the examples described below, amplified DNA was detected using a relatively slow (~1 hour) process: gel electrophoresis followed by Ethidium bromide staining, a standard method of DNA detection known to those practiced in the art. However, gas phase PCR is compatible with rapid on-line fluorescent dye-based detection (Higuchi et al., 1992) using dyes such as SYBR Green, which bind selectively to double-stranded DNA (Haugland, 1996). In principle, the double-stranded DNA reaction products of high-speed gas phase PCR can be rapidly detected on-line using reporter dyes like SYBR Green and inexpensive photodiode detectors. For example, a pressurized gas thermnocycler could be fitted with photodiode detectors and either a light-emitting diode (LED) or laser diode dye excitation source. Such optics would allow amplification/detection of DNA on an unprecedented time scale.

3. High-Speed Amplification of DNA Using a Pressurized Gas Thermocycler

Initial gas phase PCR experiments were carried out with compressed air as a "hot" gas and $CO_2$ as a "cold" gas. This configuration was not the fastest possible, but was convenient and did not require active refrigeration of the "cold" gas.

EXAMPLE 1

30 Gas Phase PCR Cycles in 5:35 (335 seconds)

The first successful DNA amplification experiments were carried out using pressurized air (36 p.s.i.) as a "hot" gas and pressurized $CO_2$ (~40 p.s.i.) as a "cold" gas in the tri-valve machine (FIG. 3a). Four model DNA templates of different lengths were PCR-armplified in separate 10 μl reactions, which were carried out in thin-walled glass capillary tubes: (a) a 91 b.p. *E.coli* O157:H7 Stx amplicon, (b) a 333 b.p. λ 'D' gene amplicon, (c) a 364 b.p Human Platelet Antigen HPA-4 amplicon, and (d) a human β-globin 536 b.p. amplicon were amplified using 30 cycles of [0 sec 92° C./0 sec 55° C./5 sec 72° C.] with pressurized air as a hot gas and $CO_2$ cooling. Gas phase PCR reactions (10 μl) were carried out thin-walled glass capillary tubes containing 50 mM Tris (pH 8.5 at 25° C.), 250 μg/ml BSA, 3 mM $MgCl_2$, 0.2 mM dNTPs, 50 pmol of forward and reverse primers, 20 picograms of template DNA, and 5 U of Taq Polymerase (Promega, Madison, Wis.). After amplification, reaction products were separated on 3% MetaPhor agarose gels w/EtBr staining. Molecular wt. markers are 67–501 b.p. long (pUC19/MspI DNA fragments).

Figure 4:
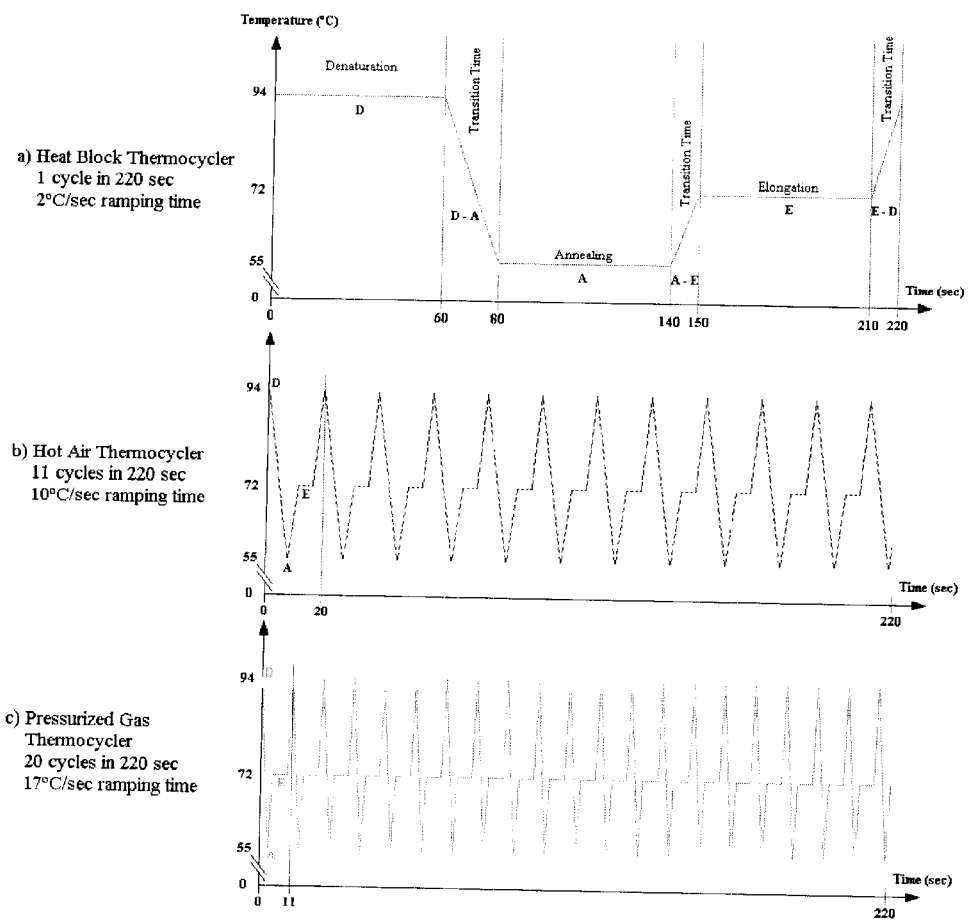
FIG. 4 shows temperature versus time profiles of different types of thermocyclers.
Figure 5A:
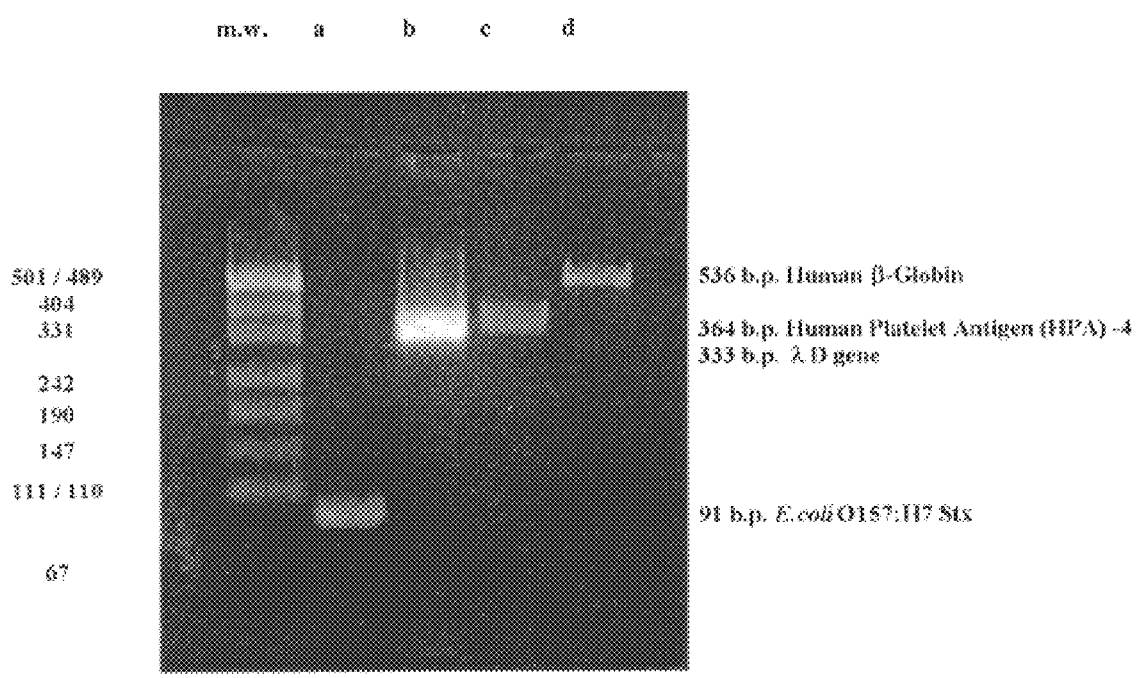
FIG. 5a is a picture of a gel electropherogram, which shows gas phase PCR amplification of four model DNA templates in 335 seconds.
Figure 5B:
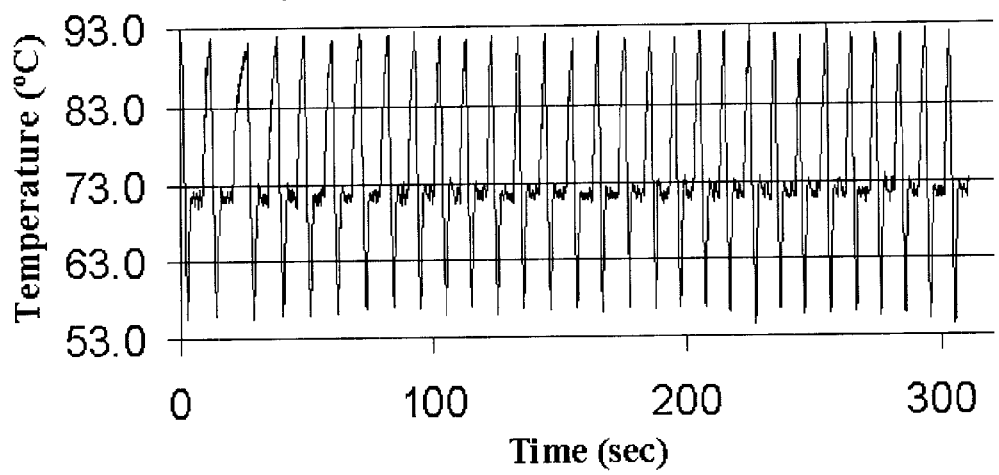

As shown in FIG. 5a, all four amplicons were amplified in high yield using gas phase PCR. The expected 536 b.p.

β-globin gene, 364 b.p. HPA-4 allele, 333 b.p. phage λ 'D' gene, and 91 b.p. *E.coli* O157:H7 Stx amplicons were amplified through 30 cycles of [0 sec 92° C. (denaturation)/0 sec 55° C. (annealing)/5 sec 72° C. (elongation)]. A low background of non-specific amplification products was observed in all four amplification reactions. In the case of the λ 'D' gene amplicon, an unusually high yield was also observed (lane b). A temperature vs. time profile of this 335 second gas phase PCR experiment showed considerable improvement in performance over any previously reported thermocycler or thermocycling method (FIGS. 4 and 5*b*).

EXAMPLE 2

Software Refinements, 30 Gas Phase PCR Cycles in 2:48 (168 seconds)

At this point, it was clear that the tri-valve apparatus was a functional therrnocycler. Not only was it very fast, but it exhibited good thermal control (±1° C.). However, its performance was limited by its software, which was written in BASIC code. Every time it needed to execute commands in response to thermal changes in the reaction chamber or heat pipe, it needed to translate from BASIC (interpreted program) to assembly code (compiled program).

A substantial amount of time (~1 sec/cycle) was lost due to this software limitation. In particular, during 30 cycles of gas phase PCR amplification, over 30 seconds of time were nonproductively lost. Consequently, the system control software was re-written in assembly code for faster operation. This modification resulted in much faster gas phase PCR, as shown in FIG. 6.

Thirty cycles of [0 sec 92° C./1 sec 55° C./1 sec 72° C.] were carried out using 36 of pressurized air with $CO_2$ cooling. Gas phase PCR reactions (10 μl) were carried out in thin-walled glass capillary tubes containing 50 mM Tris (pH 8.5 at 25° C.), 250 μg/ml BSA, 3 mM $MgCl_2$, 0.2 mM dNTPs, 50 pmol of forward and reverse primers, 20 picograms of template *E.coli* O157:H7 DNA, and 5 U of Polymerase. After amplification, reaction products were separated on 3% MetaPhor agarose gels with EtBr staining. Molecular wt. markers are 67–501 b.p. pUC19/MspI DNA fragments. Lane (a) 5 Units Taq Pol, (b) 5 Units TaqZ Pol (Takara Shuzo).

Figure 6:
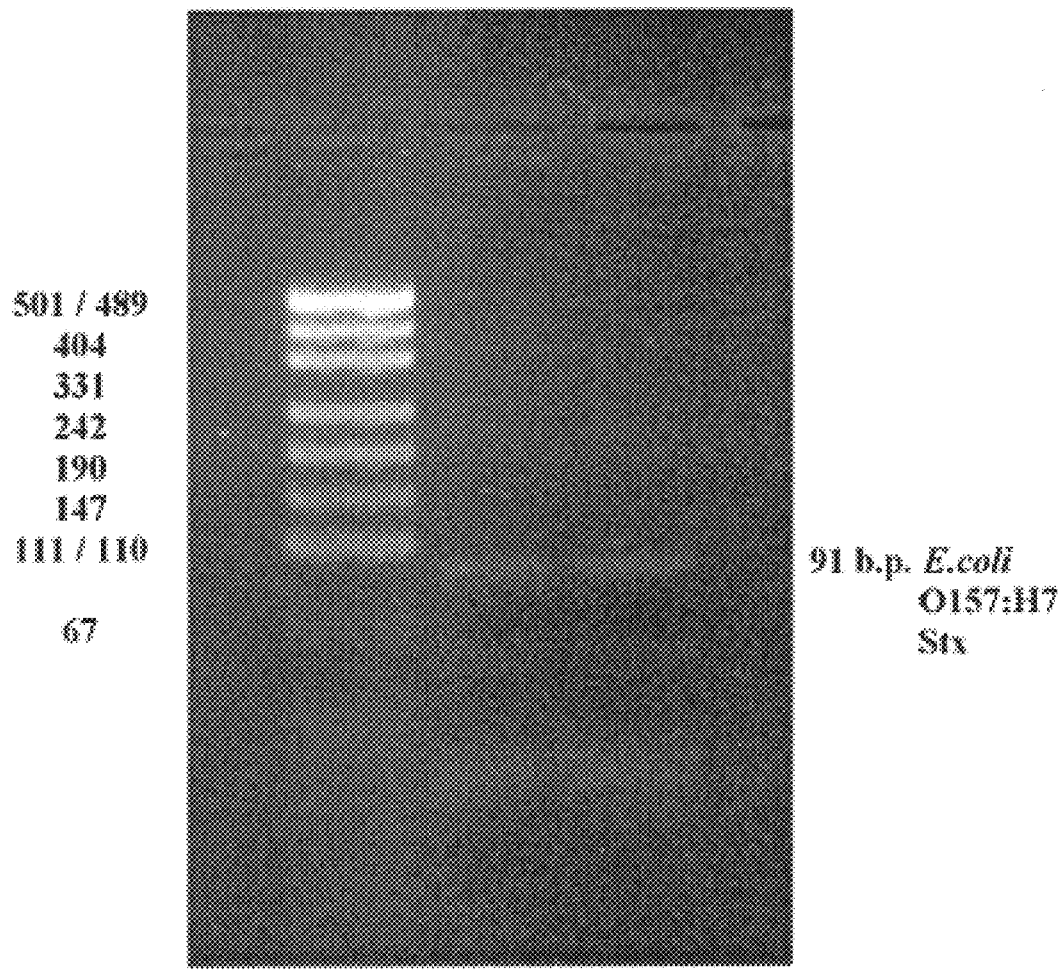
FIG. 6 is a picture of a gel electropherogram, which shows gas phase PCR amplification of a 91 b.p. DNA amplicon in 168 seconds.

FIG. 6 shows that 30 cycles of gas phase PCR can be carried out in less than 3 minutes; and that a considerable improvement in performance was achieved by writing instrument commands in assembly code. FIG. 6 also demonstrates that an infectious disease agent (*E.coli* O157:H7) could be detected using gas conditions suitable for routine analysis in many laboratories (pressurized air, bottled $CO_2$ cooling). Either Taq Pol (Promega) or a modified Taq Polymerase (TaKaRa Z-Taq™ Pol, Takara Shuzo Ltd) was suitable for rapid (<3 minute) gas phase PCR.

EXAMPLE 3

30 Gas Phase PCR Cycles in 1:53 (113 Seconds)

Even faster gas phase PCR amplification was achieved using short (<100 b.p.) amplicons. At a Taq Polymerase elongation rate of ≧80 nucleotides/sec, it was expected that ~1 sec/cycle spent during the transitions A-E+E-D (FIG. 4*a*) would be more than sufficient to copy a short 85 b.p. DNA template using a 30 mer PCR primer ($T_m$~65° C.). Accordingly, experiments were carried out with pressurized air heating/$CO_2$ cooling, using a relatively short (85 b.p.) amplicon from the *E.coli* O157:H7 verotoxin gene.

Gas phase PCR reactions (10 μl) were carried out with 36 p.s.i. of pressurized air and $CO_2$ cooling in thin-walled glass capillary tubes containing 50 mM Tris (pH 8.5 at 25° C.), 250 μg/ml BSA, 3 mM $MgCl_2$, 0.2 mM dNTPs, 50 pmol of forward and reverse primers, 20 picograms of template *E.coli* O157:H7 DNA, and 5 U of Taq Polymerase (Promega). After 30 cycles of amplification, DNAs were separated on 3% MetaPhor agarose followed by EtBr staining. M.W. markers are 67–501 b.p. long pUC19/MspI digest.

Figure 7:
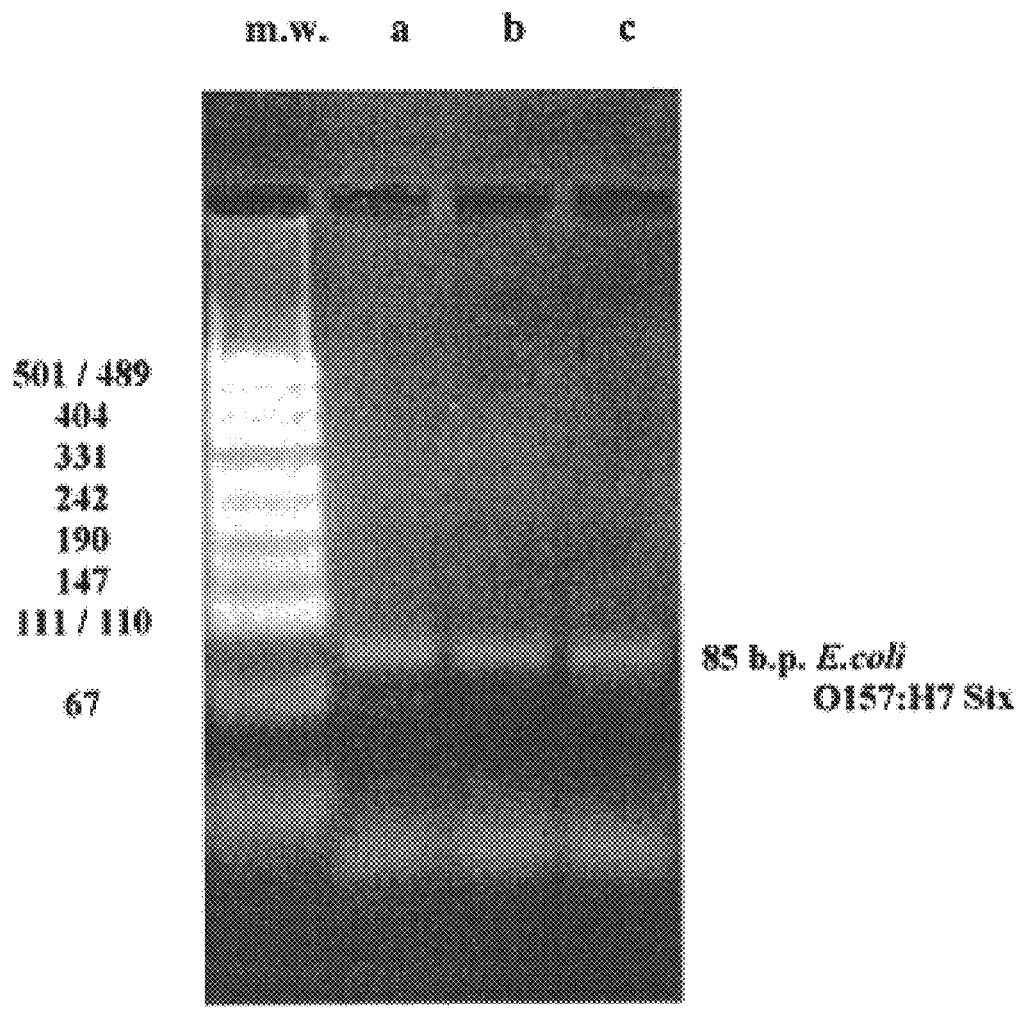
FIG. 7 is a picture of a gel electropherogram, which shows gas phase PCR amplification of an 85 b.p. DNA amplicon in 113 seconds.

FIG. 7 shows that, even with suboptimal pressurized air heating and $CO_2$ cooling, a short 85 b.p. *E.coli* O157:H7 Stx amplicon could be amplified in high yield in <2 minutes. Based upon the high heat transfer coefficient of helium gas (Ubbink, 1947; Bosworth, 1952; FIG. 1), it was hypothesized that even faster thermocycling would be possible if helium was used rather than air as a "hot" gas.

EXAMPLE 4

30 Helium Gas Phase PCR Cycles in 1:18 (78 Seconds)

A small (85 b.p.) amplicon from the *E.coli* O157:H7 Stx gene was PCR-amplified using "hot" pressurized helium gas and $CO_2$ cooling. In order to further reduce the thermocycling time, primer lengths were increased to 30 mers, so that higher annealing temperatures (62° C. to 63° C.) could be employed. In addition, the DNA denaturation temperatures were slightly reduced (86° C. to 89° C.) from those used in previous experiments.

Three different high-speed gas phase thermocycling protocols were employed: (a) [0 sec 89° C./0 sec 62° C./0 sec 72° C.]; (b) [0 sec 87° C./0 sec 62° C./0 sec 72° C.]; and (c) [0 sec 86° C./0 sec 63° C./0 sec 72° C.]. PCR reactions (10 μl) were carried out in thin-walled glass capillary tubes containing 50 mM Tris (pH 8.5 at 25° C.), 250 μg/ml BSA, 3 mM $MgCl_2$, 0.2 mM dNTPs, 50 pmol of forward and reverse primers, 20 picograms of *E.coli* O157:H7 DNA, and 5 U of Taq Polymerase (Promega, Madison, Wis.). After 30 cycles of [0 sec 89° C./0 sec 62° C./0 sec 72° C.]; (b) [0 sec 87° C.0 sec 62° C./0 sec 72° C.]; and (c) [0 sec 86° C./0 sec 63° C./0 sec 72° C.], reaction products were separated on 3% agarose gels with EtBr staining. Molecular weight markers are 67–501 b.p. long (pUC19/MspI digest).

Figure 8A:
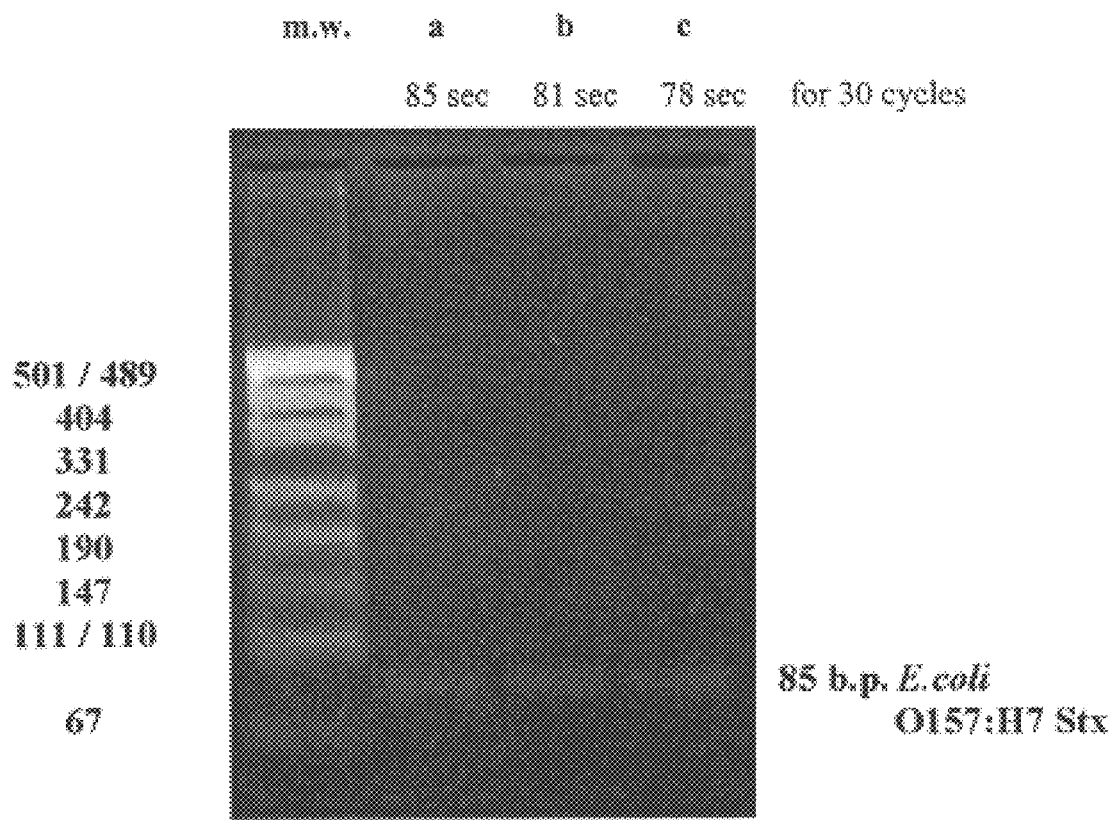
FIG. 8a is a picture of a gel electropherogram, which shows gas phase PCR amplification of an 85 b.p. DNA amplicon in 78 seconds.
Figure 8B:
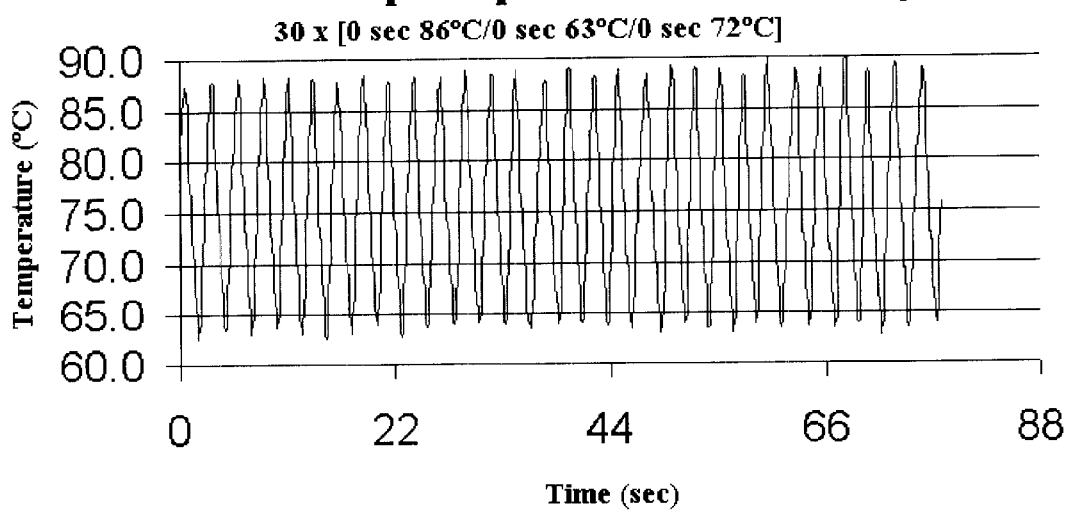

As shown in FIG. 8*a*, a high yield of the expected 85 b.p. Stx amplicon was seen in all three helium gas phase PCR reactions. FIGS. 8*a* and 8*b* demonstrate the three fastest DNA amplification reactions which have ever been carried out. The expected 85 b.p. *E.coli* O157:H7 Stx amplicon was amplified in all three reactions: (a) 1:25=85 seconds, (b) 1:21=81 seconds, (c) 1:18=78 seconds. This experiment also shows that. thermocycling was considerably faster when pressurized helium gas was used rather than air. High-speed gas phase PCR also resulted in a very low background of non-specific "haze" or false reaction products. Presumably, false priming or elongation are rare when such fast thermocycling parameters are used; there is simply no time for spurious reaction products to accumulate.

4. Summary of Results using High-Speed Gas Phase PCR

The above results can be summarized as follows: (i) A novel process, high-speed gas phase PCR, has been developed, which allows rapid amplification of DNA. (ii) A pressurized gas thermocycling apparatus has been constructed, which allows automation of the pressurized gas PCR process. (iii) Amplicons ranging in size from 85 b.p. to 536 b.p. have been successfully amplified. (iv) DNA from a heritable human disease gene (Human Platelet Antigen HPA-4 allele) and an infectious disease agent (*E.coli* O157:H7) were amplified in high yield. (v) The background of non-specific PCR reaction products was extremely low. (vi) Thermocycling was faster when hot, pressurized Helium gas was used rather than hot, pressurized air. (vii) In our fastest DNA amplification experiments, a short 85 b.p. amplicon was amplified through 30 cycles in 78 seconds.

5. Comparison to 'Ultrafast' PCR Thermocyclers

To put the speed of pressurized gas thermocyclers in perspective, the fastest experimental thermocyclers built by Lawrence Livermore National Laboratory (Northrup et al., 1998), the University of Pittsburgh (Oda et al., 1998), and the University of Washington (Friedman and Meldrum, 1998) require 8.5 to 20 minutes for 30 cycles of DNA amplification. For example, Oda et al. (1998) described "Ultrafast PCR" in which "cycle times as fast as 17 seconds could be achieved." The pressurized gas device shown in FIG. 3a requires less than 2.7 seconds/cycle; and the reaction yield is higher (see FIGS. 5a, 6, 7 and 8a). In addition, the infrared heating method used by Oda et al. is incompatible with fluorescent optical detection using >450 nm dyes and photodiode detectors.

Kopp et al. (1998) have described a miniature continuous-flow PCR device was able to amplify a 176 b.p. DNA fragment through 20 cycles in 3 to 4 minutes. However, ~$10^8$ copies of template DNA were required as starting material (Zorbas, 1999). Extrapolating from the data of Kopp et al. (1998), 30 cycles of PCR amplification would require 4.5 to 6 minutes; and the yield of amplified DNA is orders of magnitude lower than that obtained using the pressurized gas device shown in FIG. 3a.

6. Comparison to State-of-the-Art Commercial Devices.

The fastest commercially available thermocycler is manufactured by the Boehringer-Mannheim Division of Roche in Germany, under license from Idaho Technology (U.S. Pat. No. 5,455,175 to Wittwer et al.). This hot-air thermocycler requires about 9.5 minutes for 30 cycles of amplification of the 536 base pair β-globin DNA fragment. However,. with its on-line detection optics attached, the Lightcycler™ requires about 30 minutes for 30 cycles of PCR.

As shown in FIG. 8b, a pressurized gas PCR process can be used to amplify DNA ~$10^6$-fold in as little as 78 seconds. The high-speed pressurized gas thermocycling process is >20 times faster than the Roche machine and is compatible with on-line fluorescent dye-based DNA detection optics.

A general description of the present invention as well as a preferred embodiment has been set forth above. Those skilled in the art will recognize and be able to practice additional variations in the methods and devices described which fall within the teachings of this invention. Accordingly, all such modifications and additions are deemed to be within the scope of the invention which is to be limited only by the claims appended hereto.

REFERENCES CITED

U.S. PAT. NO. DOCUMENTS

| | | |
|---|---|---|
| 4,683,202 | 7/1987 | Mullis. |
| 5,187,084 | 2/1993 | Hallsby. |
| 5,455,175 | 10/1995 | Wittwer et al.. |
| 5,576,218 | 11/1996 | Zurek et al.. |
| 5,779,977 | 7/1998 | Haff et al.. |
| 5,783,439 | 7/1998 | Reichler et al.. |

Other Publications

Azbel D (1984) *Fundamentals of Heat Transfer for Process Engineering*, Noves Publications, Park Ridge, N.J., pp 12–20.

Bosworth R C L (1952) *Heat Transfer Phenomena: the Flow of Heat in Physical Systems*, John Wiley & Sons, Inc., New York, Chapter II, "The Thermal Conductivity of Gases," pp. 23–41.

Chapman A J (1984) *Heat Transfer*, Fourth Edition, The Macmillan Company, New York. Erlich H A, ed. (1989) *PCR Technology: Principles and Applications for DNA Amplification*, Stockton Press, New York.

Fourier J B J (1822) *Théorie Analytigue de la Chaleur*, Fermin Didot, Paris. Translated by A. Freeman (1988) as *The Analytical Theory of Heat*, Dover Paperback Books, New York.

Friedman N A and Meldrum D R (1998) "Capillary tube resistive thermal cycling." Anal. Chem. 70: 2997–3002.

Gelfand D H and White T J (1990) "Thermostable DNA Polymerases." In: M A Innis, D H Gelfand, J J Sninsky, and T J White, eds., *PCR Protocols: a Guide to Methods and Applications*, Academic Press, Inc., San Diego.

Haugland R P (1996) "Nucleic Acid Stains," in *Handbook of Fluorescent Probes and Research Chemicals*, Sixth Edition, Molecular Probes, Inc., Eugene Oreg., pp.144–150.

Higuchi R, Dollinger G, Walsh S P, and Griffith R (1992) "Simultaneous amplification and detection of specific DNA sequences." Bio/Technology 10: 413–417.

Idaho Technology, Inc. (1995) The Rapid Cyclist 3(1): 16, Idaho Falls, Id.

Innis, M A, Myambo K B, Gelfand D H, and Brow M A D (1988) "DNA sequencing with *Thermus aquaticus* DNA polymerase and direct sequencing of polymerase chain-reaction amplified DNA." Proc. Nat. Acad. Sciences USA 85: 9436–9440.

Johnson B (1998) "The Competition Heats Up. The annual review of thermal cyclers takes a sneak peak at the new products for 1998." The Scientist, 12 (24): "Thermnal Block Table."

Johnston H L and Grilly E R (1946) "The thermal conductivities of eight common gases between 80° and 380° K," J. Chem. Physics 14: 233–238.

Kogan S C, Doherty M, and Gitschier J (1987) "An improved method for prenatal diagnosis of genetic diseases by analysis of amplified DNA sequences." New Eng. J. Med. 317: 985–990.

Kopp M U, Mello A J, and Manz A (1998) "Chemical amplification: continuous-flow PCR on a chip." Science 280: 1046–1048.

Mullis K, Ferré F, and Gibbs R A, eds. (1994) *The Poly-Merase Chain Reaction*, Birkhauser, Boston.

Newton C R (1995) "PCR Instruments," In: C R Newton, *Essential PCR Data*, John Wiley & Sons, Chichester, England, pp. 12–23.

Northrup M A, Benett B, Hadley D, Landre P, Lehew S, Richards J, and Stratton P (1998) "A miniature analytical instrument for nucleic acids based on micromachined silicon reaction chambers." Anal. Chem 70: 918–922.

Oda R P, Strausbauch M A, Hubmer A F, Jurrens S R, Craighead J, Wettstein P J, Eckloff B, Kline B, and Landers J P (1998) "Infrared-mediated thermocycling for ultrafast polymerase chain reaction ampli-fication of DNA." Anal. Chem. 70: 4361–4368.

Oste C C (1989) "PCR Automation." In: Erlich H A, ed., *PCR Technology: Principles and Applications for DNA Amplification*, Stockton Press, New York, pp. 23–30.

Oste C C (1994) "PCR Instrumentation: Where Do We Stand?" In: Mullis, Ferré, and Gibbs, eds. (1994) *The PolyMerase Chain Reaction*, Birkhauser, Boston, pp. 165–173.

Persing D H, Smith T F, Tenover F C, and White T J, eds. (1993) *Diagnostic Molecular Biology: Principles and Applications*, ASM Press, Washington, D.C.

Saiki R K, Scharf S, Faloona F, Mullis K B, Horn G T, Erlich H A and Arnheim N (1985) "Enzymatic amplification of beta-globin genomic sequences and restriction site analysis for diagnosis of sickle cell anemia." Science 230: 1350–1354.

Saiki R K, Walsh P S, Levenson P H, and Erlich H A (1989a) "Genetic analysis of amplified DNA with immobilized sequence-specific oligonucleotide probes" Proc. Nat. Acad. Sciences USA 86: 6230–6234.

Saiki R K (1989b) "The design and optimization of the PCR." In: *PCR Technology: Principles and Applications for DNA Amplification*, H A Erlich, ed. Stockton Press, New York, pp. 17–22.

Ubbink J B (1947) "Thermal conductivity of gaseous helium." Physica 13: 629–634; 659–668.

Wittwer C T, Filmore G C, and Hillyard D R (1989) "Automated polymerase chain reaction in capillary tubes with hot air." Nucleic Acids Research 17: 4353.

Wittwer C T, Filmore G C, and Garling D J (1990) "Minimizing the time required for DNA amplification by efficient heat transfer to small samples." Anal. Biochem. 186: 328–331.

Wittwer C T and Garling D J (1991) "Rapid cycle amplification: Time and temperature optimization." BioTechniques 10: 76–83.

Wittwer C T, Reed G B, and Ririe K M (1994) "Rapid Cycle DNA Amplification." In: Mullis, Ferré, and Gibbs, eds., *The Polymerase Chain Reaction*, Birkhauser, Boston, pp. 174–181.

Zorbas H (1999) "Miniature Continuous-Flow Polymerase Chain Reaction: A Breakthrough?" Angew. Chem. Int. Ed. 38: 1055–1058.

What is claimed and desired to be secured by United States Letters Patent is:

1. A process for amplifying DNA, comprising:
   (a) providing a reaction chamber containing a biological sample having DNA, a DNA polymerase, oligonucleotide primers, and deoxynucleotide precursors, the reaction chamber accepting the flow of one or more heat transfer gases;
   (b) heating a first heat transfer gas in a heat chamber that is physically separated from the reaction chamber;
   (c) delivering the first heat transfer gas to the reaction chamber at a pressure of at least 20 psi to about 100 psi, wherein heat is transferted from the first heat transfer gas to the DNA to denature the DNA;
   (d) delivering a second heat transfer gas at a pressure of at least 20 psi to the reaction chamber at a pressure of at least 20 psi to cool the reaction chamber to a temperature where the denatured DNA is annealed to the oligonucleotide primers; and
   (e) increasing the temperature of the reaction chamber to a temperature sufficient to allow for elongation of primer:template complexes.

2. The process of claim 1, further comprising:
   (f) repeating steps (c) through (e) until a desired quantity of amplified DNA has been produced.

3. The process of claim 1, wherein an electronic valve is utilized to regulate the flow of the first heat transfer gas from the heat chamber to the reaction chamber.

4. The process of claim 1, wherein the first heat transfer gas and the second heat transfer gas are the same type of gas.

5. The process of claim 1, wherein the first heat transfer gas and the second heat transfer gas are different types of gas.

6. The process of claim 1, wherein the second heat transfer gas is at a pressure greater than one atmosphere.

7. The process of claim 1, wherein the first heat transfer gas is air.

8. The process of claim 1, wherein the first heat transfer gas is selected from the group consisting of helium, nitrogen, and mixtures thereof.

9. The process of claim 1, wherein the first heat transfer gas is selected from the group consisting of hydrogen, neon, methane, argon, krypton, carbon dioxide, and mixtures thereof.

10. The process of claim 1, wherein the second heat transfer gas is carbon dioxide.

11. The process of claim 1, wherein the second heat transfer gas is selected from the group consisting of air, hydrogen, neon, methane, argon, krypton, carbon dioxide, and mixtures thereof.

12. The process of claim 1, wherein the second heat transfer gas is actively cooled to a temperature less than ambient air temperature prior to delivering the second heat transfer gas to the reaction chamber.

13. The process of claim 1, wherein the reaction chamber has a heat transfer coefficient of less than 0.5 Watts/centimeter-degree K.

14. The process of claim 1, wherein electronic valves under the control of a microprocessor are used to regulate the flow of the first and second heat transfer gases into the reaction chamber.

15. The process of claim 1, wherein elongation by DNA polymerase is the rate-limiting step.

16. The process of claim 14, wherein digital relays are employed to actuate the electronic valves.

17. A process for amplifying DNA, comprising:
   (a) providing a reaction chamber containing a biological sample having DNA, a DNTA polymerase, oligonucleotide primers, and deoxynucleotide precursors, the reaction chamber having a pressure;
   (b) heating helium gas in a heat chamber that is physically separated from the reaction chamber;
   (c) delivering the heated helium gas to the reaction chamber at a pressure of at least 20 psi to about 100 psi, wherein heat is transferred from the helium gas to the DNA to denature the DNA;
   (d) delivering a cooling gas to the reaction chamber at a pressure of at least 20 psi to cool the reaction chamber to a temperature where the denatured DNA is annealed to the oligonucleotide primers; and
   (e) increasing the temperature of the reaction chamber to a temperature sufficient to aflow for elongation of primer:template complexes.

18. The method of claim 17, wherein the cooling gas is carbon dioxide.

* * * * *